United States Patent [19]

Kitano et al.

[11] Patent Number: 4,935,356
[45] Date of Patent: Jun. 19, 1990

[54] PRODUCTION OF INTERLEUKIN-2

[75] Inventors: Kazuaki Kitano, Sakai; Shigeru Fujimoto, Ikeda, both of Japan

[73] Assignee: Takeda Chemical Industries, Ltd., Osaka, Japan

[21] Appl. No.: 302,064

[22] Filed: Jan. 24, 1989

Related U.S. Application Data

[63] Continuation of Ser. No. 185,307, Apr. 20, 1988, abandoned, which is a continuation of Ser. No. 835,765, Feb. 27, 1986, abandoned.

[30] Foreign Application Priority Data

Mar. 11, 1985 [JP] Japan .................................. 60-48698

[51] Int. Cl.$^5$ ...................... C12P 21/02; C12P 21/00; C12N 1/38; C12N 1/20; C07K 13/00; C07K 13/26
[52] U.S. Cl. .................................. 435/69.52; 435/244; 435/252.33; 435/253.6; 530/351; 935/61; 935/66; 935/73
[58] Field of Search ................. 435/68, 70, 243, 244, 435/252.33, 253.6, 813, 849; 530/351; 935/29, 61, 66, 73

[56] References Cited

U.S. PATENT DOCUMENTS

| 4,021,304 | 5/1977 | Shimamatsu et al. | 195/28 R |
|---|---|---|---|
| 4,357,422 | 1/1982 | Giard et al. | 435/68 |
| 4,391,907 | 7/1983 | Matsui et al. | 435/115 |
| 4,499,188 | 2/1985 | Konrad et al. | 435/70 |
| 4,569,790 | 2/1986 | Koths et al. | 435/68 |

FOREIGN PATENT DOCUMENTS 145390  6/1985  European Pat. Off. .

OTHER PUBLICATIONS

Queen, C. (1983) J. Mol. Appl. Genet, 2, 1–10.

Primary Examiner—Thomas G. Wiseman
Assistant Examiner—Charles L. Patterson
Attorney, Agent, or Firm—Ernest V. Linek; David G. Conlin

[57] ABSTRACT

The present invention provides an improvement in a method for producing interleukin-2 by cultivating a transformant of *Escherichia coli* capable of producing interleukin-2 into a medium, which comprises inoculating said *Escherichia coli* into the medium of pH from about 4.8 to 6.0 and growing it while maintaining this pH range.

By the method of the present invention, the interleukin-2 productivity is considerably improved.

14 Claims, 2 Drawing Sheets

```
       1
X- Ala Pro Thr Ser Ser Ser Thr Lys Lys Thr Gln Leu Gln
                              20
   Leu Glu His Leu Leu Leu Asp Leu Gln Met Ile Leu Asn

Gly Ile Asn Asn Tyr Lys Asn Pro Lys Leu Thr Arg Met
40
   Leu Thr Phe Lys Phe Tyr Met Pro Lys Lys Ala Thr Glu
                              60
   Leu Lys His Leu Gln Cys Leu Glu Glu Glu Leu Lys Pro

Leu Glu Glu Val Leu Asn Leu Ala Gln Ser Lys Asn Phe
     80
   His Leu Arg Pro Arg Asp Leu Ile Ser Asn Ile Asn Val
                             100
   Ile Val Leu Glu Leu Lys Gly Ser Glu Thr Thr Phe Met

Cys Glu Tyr Ala Asp Glu Thr Ala Thr Ile Val Glu Phe
          120
   Leu Asn Arg Trp Ile Thr Phe Cys Gln Ser Ile Ile Ser
       133
   Thr Leu Thr
```

Fig. 1.

```
5' GGGGGGGGGGGGGGGGGGATCACTCTCTTTAATCACTACTCACAGTAACC

S1
   TCAACTCCTGCCACA ATG TAC AGG ATG CAA CTC CTG TCT TGC

S20  1
   ATT GCA CTA AGT CTT GCA CTT GTC ACA AAC AGT GCA CCT

ACT TCA AGT TCT ACA AAG AAA ACA CAG CTA CAA CTG GAG

20
   CAT TTA CTG CTG GAT TTA CAG ATG ATT TTG AAT GGA ATT

40
   AAT AAT TAC AAG AAT CCC AAA CTC ACC AGG ATG CTC ACA

TTT AAG TTT TAC ATG CCC AAG AAG GCC ACA GAA CTG AAA

60
   CAT CTT CAG TGT CTA GAA GAA GAA CTC AAA CCT CTG GAG

80
   GAA GTG CTA AAT TTA GCT CAA AGC AAA AAC TTT CAC TTA

AGA CCC AGG GAC TTA ATC AGC AAT ATC AAC GTA ATA GTT

100
   CTG GAA CTA AAG GGA TCT GAA ACA ACA TTC ATG TGT GAA

TAT GCT GAT GAG ACA GCA ACC ATT GTA GAA TTT CTG AAC

120
   AGA TGG ATT ACC TTT TGT CAA AGC ATC ATC TCA ACA CTG

133
   ACT TGA TAATTAAGTGCTTCCCACTTAAAACATATCAGGCCTTCTATTT

ATTTAAATATTTAAATTTTACCCCCCCCCCCCCCC 3'
```

Fig. 2.

PRODUCTION OF INTERLEUKIN-2

This is a continuation of co-pending application Ser. No. 185,307 filed on Apr. 20, 1988.

BACKGROUND OF THE INVENTION

The present invention relates to a method for producing interleukin-2.

Interleukin-2 [hereinafter abbreviated IL-2, which is also called T-cell growth factor (TCGF)] is a lymphokine produced by T-cells stimulated by lectin, allotype antigens, etc. [Science, Vol. 193, p. 1007 (1976)].

Using IL-2, a great number of clones of killer T-cells, helper T-cells, natural killer cells etc. have been obtained [e.g. Nature, Vol. 268, p. 154 (1977)]. In addition to such killer cells, IL-2 can be used in the preferential proliferation in vitro of antigen-specific killer T-cells, which recognize and destroy specific antigens such as tumor antigens. It is also possible to inhibit tumor growth by transferring thus proliferated tumor-specific killer T-cells into animals [The Journal of Immunology, Vol. 125, p. 1904 (1980)].

These experimental facts suggest the great potential for the application of IL-2 as an antitumor agent. It is also known that IL-2 promoted recovery of the helper T-cell function in nude mice lacking thymic function [European Journal of Immunology, Vol. 10, p. 719 (1980)] and recovery of the induction of killer T-cells to said helper T-cells [Nature, Vol. 284, p. 278 (1980)]; it is expected that IL-2 will also be applied in the therapy of immunodeficiency diseases.

Human IL-2 can be obtained from human T-cells, but only in extremely small quantities. Owing to the recent progress of gene recombination technology, however, it has become possible to obtain human IL-2 as a bioactive protein from a culture of *Escherichia coli*, of *Escherichia coli* etc. possessing expression vectors to which a human IL-2 gene has been transferred [Nature, Vol. 302, p. 305 (1983); Nucleic Acids Research, Vol. 11, p. 4307 (1983)].

Conventional human IL-2 production methods are not generally favorable for industrial applications because of their low human IL-2 productibility.

In view of this, the present inventors studied the cultivation methods for *E. coli* possessing IL-2 productibility, finding that such productibility is considerably improved by culturing *E. coli* under acidic pH conditions of from about 4.8 to 6, this despite the fact that fermentation of *E. coli* had typically been carried out under neutral pH conditions of approx. from 6.5 to 7.5 as it was generally regarded that neutral or slightly alkaline conditions were preferred [Biochemical Engineering, University of Tokyo Press, 25–26 (1965)].

Based on this finding, the inventors made further studies, developing the present invention.

SUMMARY OF THE INVENTION

The present invention provides an improvement in a method for producing interleukin-2 by cultivating a transformant of *Escherichia coli* capable of producing interleukin-2 in a medium, which comprises inoculating said *Escherichia coli* into the medium at a pH of from about 4.8 to 6.0 and growing it while maintaining that pH range.

BRIEF EXPLANATION OF THE DRAWINGS

FIG. 1 shows the amino acid sequence (X indicates Met or hydrogen) of human IL-2.

FIG. 2 shows an example of DNA sequence of the human IL-2 gene.

DETAILED DESCRIPTION OF THE PREFERRED EMBODIMENTS

The said *E. coli* possessing IL-2 productibility has IL-2 genes which may be obtained by standard gene recombination techniques, or a DNA-coding for polypeptide having a physiological activity similar to that of IL-2.

The use of mammalian derived IL-2 genes is recommended, preferably a gene coding for the amino acid sequence (No. 1 to No. 133) of human IL-2, as shown in FIG. 1. For example, the base sequence (codon No. 1 to No. 133) as shown in FIG. 2 may be used.

The following DNAs are included among those coding for polypeptides having physiological activities similar to IL-2: a DNA in which the codon coding for cysteine (e.g. No. 125 cysteine) in the amino acid sequence shown in FIG. 1 has been replaced by a codon coding for serine or threonine, and a DNA in which the fragment coding for the four amino acids at the N-terminus in the same amino acid sequence has been removed [Japanese Patent Publication (laid open) No. 126088/1985].

It is preferable that said gene (DNA) has a promoter or promoters upstream therefrom; applicable promoters include the tryptophane (trp) promoter, the lactose (lac) promoter, the protein chain elongation factor Tu (tuf B) promoter, and the rec A promoter etc. The trp promoter affords particularly favorable results when used in the present invention.

The above-mentioned genes (DNAs) and promoters are usually transferred to a vector for use as expression plasmids, one of the most common of which is pBR 322, a derivative of Col El [Gene, Vol. 2, p. 95 (1977)]. However, other plasmids can be used as long as they can be replicated and retained within *E. coli* cells; for example: pBR 313 [Gene, Vol. 2, p. 75 (1977)]; pBR 324 and pBR 325 [Gene, Vol. 4, p. 121 (1978))]; pBR 327 and pBR 328 [Gene, Vol. 9, p. 287 (1980)]; pKY 2289 [Gene, Vol. 3, p. 1 (1978)]; pKY 2700 [Biochemistry, Vol. 52, p. 770 (1980)]; pACYC 177 and pACYC 184 [Journal of Bacteriology, Vol. 134, p. 1141 (1978)]; and pRK 248, pRK 646 and pDF41 [Methods in Enzymology, Vol. 68, p. 268 (1979)].

Bacteriophages, e.g., the gt. C phage [Proceedings of National Academy of Science, USA, Vol. 71, p. 4579 (1974)], the gt. B phage [ibid., Vol. 72, p. 3416 (1975)] and the Dam phage [Gene, Vol. 1, p. 255 (1977)] belonging to gt systems, Charon vector [Science, Vol. 196, p. 161 (1977); Journal of Virology, Vol. 29, p. 555 (1979)], and vectors using filamentous phages, may likewise be used as expression vectors.

Said expression plasmids may be constructed using conventional methods [Nature, Vol. 302, p. 305 (1983); Nucleic Acids Research, Vol. 11, p. 4307 (1983)].

*Escherichia coli* is used as the host bacteria to which an expression plasmid integrated with a human IL-2 gene is transferred; those deriving from *E. coli* K-12 strain are particularly desirable from the point of view of handling and safety. For example, *E. coli* strains PR 13, C-4, 294, DH 1, W 3110 and C 600 produce favorable results.

*E. coli* C-4 is a strain isolated from *E. coli* PR 13 strain [Journal of Bacteriology, Vol. 97, p. 1522 (1969)], a derivative of the K-12 strain (parent strain). It has the following bacteriological characteristics:

C-4 Strain Bacteriological Characteristics (a) Microscopic factors
 (1) Shape and size: Like normal *E. coli* K-12 strain, a single- or double-type bacillus of $0.5$–$1.0 \times 2$–$5$ μm, exhibiting no polymorphism.
 (2) Motility: Yes
 (3) Flagella: Peritrichous
 (4) Gram-strain: Negative
 (5) Sporulation: No
 (6) Acid fastness: Non-acid-fast (b) Growth state on various media
 (1) Meat broth agar plate culture: Colonies are small, flat, circular, translucent and lustrous.
 (2) Meat broth agar slant culture: Colonies are medium-sized, flat, translucent and slightly lustrous.
 (3) Meat broth liquid culture: Growability is medium. Forms uniform suspension.
 (4) Meat broth gelatin stab culture: Grows in uniformly diffused state, causing no gelatin liquefication.
 (5) Litmus milk: Not coagulated or peptonized. pH is also unchanged.

(c) Physiological characteristics
 (1) Nitrate reduction: Positive
 (2) Denitrification: Negative
 (3) MR test: Positive
 (4) VP test: Negative
 (5) Indole production: Positive
 (6) Hydrogen sulfide production: Negative
 (7) Starch hydrolysis: Negative
 (8) Citric acid utilization: Negative
 (9) Inorganic nitrogen source utilization:
  (i) Sodium nitrate: Positive
  (ii) Ammonium sulfate: Positive
 (10) Chromogenicity: Water-soluble pigment production is not found.
 (11) Urease: Negative
 (12) Oxidase: Negative
 (13) Catalase: Negative
 (14) Growable conditions:
  (i) pH: 4.5–10.0
  (ii) Temperature: 18°–47° C.
 (15) Behavior in oxygen: Facultatively anaerobic
 (16) O-F test: Positive
 (17) Acidogenicity and aerogenicity from various saccharides (Table 1)

TABLE 1

| Saccharide | Acidogenicity | Aerogenicity |
|---|---|---|
| L-arabinose | + | + |
| D-xylose | − | − |
| D-glucose | + | + |
| D-mannose | + | + |
| D-fructose | + | + |
| D-galactose | − | − |
| Maltose | − | − |
| Sucrose | − | − |
| Lactose | + | + |
| Trehalose | + | + |
| D-sorbitol | + | + |
| D-mannitol | − | − |
| Inositol | − | − |
| Glycerol | + | + |
| Starch | − | − |

This strain (*Escherichia coli* C-4) which was deposited under FERM P-8101 on Feb. 16, 1985 at the Fermentation Research Institute, Agency of Industrial Science and Technology, Ministry of International Trade and Industry (FRI), the deposit being converted to a deposit under the Budapest Treaty, has been stored at FRI under FERM BP-966, and under IFO-14421 at the Institute for Fermentation, Osaka (IFO).

*E. Coli* 294 is a known strain [Proceedings of National Academy of Science, USA, Vol. 73, p. 4474 (1976)], and also has been deposited under IFO-14171 at IFO.

W 3110 and C 600 also are known strains; they are respectively listed under ATCC 27325 and ATCC 23724 in the ATCC Catalogue of Strains, Vol. 1, 15th edition, 1982.

DH 1 strain is described in Nature, Vol. 217, p. 1110 (1968).

*E. coli* cells capable of producing IL-2 can be produced by using expression plasmids to transform host *E. coli* cells; this transformation can be made using conventional methods, such as those described in the Journal of Molecular Biology, Vol. 53, p. 159 (1970), Methods in Enzymology, Vol. 68, p. 445 (1979), and Gene, Vol. 3, p. 279 (1978).

*E. coli* transformed to produce IL-2 is inoculated into a medium of pH 4.8 to 6.0 and cultured therein while maintaining this range. A pH range of 5.0 to 5.8 is more preferred; a pH value of approx. 5.5 is particularly conducive to this culturing.

After sufficient growth, however, culture conditions may be shifted out of this pH range, e.g., to more acidic conditions.

The medium pH may be adjusted using an inorganic base or a mineral acid before or after the medium is prepared and sterilized. pH adjustment may be required during *E. coli* cultivation to maintain pH within the specified range. Since pH usually decreases during cultivation, pH is adjusted by adding an inorganic base, e.g. ammonia, sodium hydroxide, and sodium carbonate; however, mineral acids such as sulfuric acid may be added, if desired. Of these substances, about 10 to 20% aqueous ammonia is especially preferable as it constitutes a nitrogen source for the media.

As a medium, M-9 medium and M-03 medium, which are supplemented with glucose and casamino acid, [medium compositions are shown in Table 2] are usually used. Those are not the only applicable media, however; any medium may be used as long as IL-2 may be produced therein. In cases of recombinant integrating promoters such as the trp promoter, agents such as 3-β-indolylacrylic acid may be added to increase promoter efficiency. Substances such as glucose and casamino acid may also be added during cultivation, if required. To proliferate recombinant *E. coli* cells preferentially, agents (e.g., tetracycline, etc.) to which these cells exhibit a resistance may be used according to the types of genes retained in their plasmids.

TABLE 2

| Component | Examples of Applicable Media | |
|---|---|---|
| | Modified M-9 Medium | M-03 Medium |
| Glucose | 10 g/l | 10 g/l |
| Na$_2$HPO$_4$ | 6 g/l | — |
| KH$_2$PO$_4$ | 3 g/l | 3 g/l |
| NaCl | 0.5 g/l | 0.5 g/l |
| NH$_4$Cl | 1 g/l | 1 g/l |
| MgSO$_4$.7H$_2$O | 0.34 g/l | 0.34 g/l |
| Casamino acid | 10 g/l | 10 g/l |

Culture temperature is usually from about 15° to 45° C. A considerably higher productivity may be obtained by changing the temperature as follows: temperature is kept at around 37° C. until the middle stage of the growth, and is then lowered to between about 20°–30° C. in proportion to the propagation.

Cultivation under aeration with agitation is usually employed. It may be more favorable to keep the oxygen concentration of the medium at approx. 5% (v/v) or more, e.g., a saturated oxygen concentration, as this increases IL-2 production quantity. It may be also effective to use pure oxygen combined with air during cultivation.

The quantity of IL-2 produced using the method of the present invention above may be determined using IL-2 dependent cell lines. It is known that human IL-2 promotes the proliferation of rat and mouse IL-2 dependent cells as well as that of human IL-2 dependent cells [Immunological Review, Vol. 51, p. 257 (1980)]; thus human, rat or mouse IL-2 dependent cells lines may be used [Journal of Immunology, Vol. 130, pp. 981–988 (1983)].

Mouse IL-2 dependent cell lines produce particularly stable subculturing over a long period; highly reproducible data may thus be obtained using them.

In the present specification, the quantity of IL-2 produced was measured using IL-2 dependent mouse cells, in accordance with the method in which the uptake of radioactive thymidine by IL-2 dependent mouse cells is used as an indicator [Biochemical Biophysical Research Communications, Vol. 109, p. 363 (1982)].

Various methods may be used to extract IL-2 produced by the present invention from cultured cells. For example: (1) Cultured bacterial cells are collected by a conventional method, and suspended in a buffer solution containing a protein denaturing agent, such as guanidine hydrochloride. The resulting suspension, after stirring under cool conditions, is centrifuged, yielding a supernatant containing IL-2. (2) Collected cultured cells are suspended in a buffer solution. After the cells are destroyed by ultrasonication, lysozyme treatment and/or freezing-thawing, the resulting suspension is centrifuged, yielding a supernatant containing IL-2.

Conventional separation and purification methods may be used in combination to separate IL-2 from the above supernatants and purify it. Applicable methods include the followings: methods based on solubility, e.g., salting-out and solvent precipitation; those based mainly on molecular weight difference, e.g., dialysis, ultrafiltration, gel filtration and SDS-polyacrylamide gel electrophoresis; those based on electric charge difference, e.g., ion exchange chromatography; those based on specific affinity, e.g. affinity chromatography; those based on hydrophobicity difference, e.g., reversed-phase HPLC; and those based on isoelectric point difference, e.g., isoelectric electrophoresis. Since human IL-2 protein is highly hydrophobic, hydrophobic-column chromatography, particularly that using a reversed-phase type column, is eminently efficient in the purification of said protein.

IL-2 protein purified as described above attains the preferential proliferation in vitro of antigen-specific killer T-cells which recognize and destroy tumor antigens etc., and natural killer cells which destroy tumors independent of antigen sensitization. In addition, when these killer T-cells are transferred to a living body, human IL-2 produced by the present invention is inevitably inoculated simultaneously, improving the antitumor efficiency of these cells. For these reasons, said IL-2 protein may be used in the prevention of oncogenesis, the treatment of tumors and therapy of immunodeficiency diseases, and in warm-blooded animals, e.g., mice, rats, rabbits, dogs, cats, pigs, horses, sheep, cattle, and man.

Said IL-2 protein, when used as a preventive/therapeutic drug for tumors, may be given by oral or parenteral administration in the form of an injection, capsule, etc., after being diluted with well-known carriers. In addition, its single and combination use with killer T-cells or natural killer cells proliferated in vitro as stated previously is possible.

Furthermore said IL-2 protein, which has a bioactivity similar to that of well-known natural human IL-2, may be used in the same manner; it is sufficiently effective even at an extremely low dose, as its dissociation constant from cellular IL-2 receptors is quite small.

The present invention is hereinafter described in more detail with examples of preferred embodiments and a reference example.

Representative transformants shown in the following examples have been registered at the Fermentation Research Institute, Agency of Industrial Science and Technology, Ministry of International Trade and Industry (FRI) and Institute for Fermentation, Osaka (IFO) under the deposit numbers shown in the following table.

| Transformant | Deposit Organization FRI (Deposited date) | IFO |
|---|---|---|
| Escherichia coli C-4/pTF4 | FERM BP-967 (Feb. 16, 1985) | IFO-14422 |
| Escherichia coli DH1/pTF4 | FERM BP-628 (Apr. 6, 1984) | IFO-14299 |

EXAMPLE 1

Expression plasmid pTF, which contains a human IL-2 structural gene, was isolated from *E. coli* DH1/pTF4 (FERM BP-628) [European Patent Publication (laid open) No. 145390] in accordance with the method of Birnboim, H. C. et al. [Nucleic Acids Research, Vol. 7, p. 1513 (1979)]. Using said plasmid, *E. coli* PR 13 (described previously) was transformed in accordance with the method of Cohen, S.N. et al. [Proceedings of the National Academy of Science, USA, Vol. 69, p. 2110 (1972)]. The resulting transformant cells were inoculated into media (50 ml, pH 7.0) containing 1% Bacto-tryptone (Difco Laboratories, USA), 0.5% Bacto-yeast Extract (same as above), 0.5% sodium chloride and 5 mg/l tetracycline hydrochloride in a conical flask of 200 ml capacity, and then cultured at 37° C. for one night. Each resulting culture liquid was then inoculated into a 200 ml conical flask containing a medium (30 ml) prepared by adding 1 mg/l vitamin $B_1$ hydrochloride to an modified M-9 medium, after which it was continuously cultured at 37° C. for 4 hours, at 30° C. for 4 hours and at 25° C. for 10 hours; a strain possessing an eminently high IL-2 productibility, i.e. *E. coli* C-4/pTF4, was selected.

The resulting *E. coli* C-4/pTF4 strain cells were inoculated into media (50 ml, pH 7.0) containing 1% Bacto-trypton (Difco Laboratories, USA), 0.5% Bacto-yeast Extract (same as above), 0.5% sodium chloride and 5 mg/l tetracycline hydrochloride in a conical flask of 250 ml capacity and cultured at 37° C. for one night, yielding an original culture liquid. Separately, 2.5 l of a medium prepared by adding 1 mg/l vitamin $B_1$ hydrochloride to M-03 medium was placed in 8 jar fermenters of 5 l capacity; the pH of each medium, after sterilization, was adjusted to 7.5, 7.0, 6.5, 6.0, 5.5, 5.0, 4.8, or 4.5 with about 10-20% aqueous ammonia or 5N sulfuric acid. To each of the resulting pH-adjusted media, 125 ml of the original culture liquid was inoculated and cultured at 37° C., 2.5 l/min. of aeration rate and 1300 rpm of agitation stir rate, with specified pH value maintained using ammonia water or 5N sulfuric acid. When glucose content decreased to 0.5% during culture, 1% glucose and 1% casamino acid were added and cultures were continued; the results are shown in Table 3. IL-2 productibility in the pH range of 4.8-6.0 increased 2-5 times over that obtained at pH 7.0 (i.e., the usually adopted pH value).

TABLE 3

Effect of Culture pH on IL-2 Productibility
(Culture at 37° C.)

| pH | IL-2 Productibility* |
|---|---|
| 4.5 | 15 |
| 4.8 | 240 |
| 5.0 | 400 |
| 5.5 | 520 |
| 6.0 | 330 |
| 6.5 | 150 |
| 7.0 | 100 |
| 7.5 | 50 |

*Indicated as percentage relative to the productibility obtained at pH 7.

EXAMPLE 2

Eight media of different pH were prepared in the same manner as in Example 1, in which aliquots of an original culture liquid obtained as in Example 1 were subjected to cultivation with aeration and agitation for 24 hours with only the culture temperature changing. That is, starting at the 37° C., culture temperature was lowered to 30° C. when growth reached a level of 500 Klett units, and further lowered to 25° C. when growth reached a level of 1000 klett units; cultivation was conducted for 24 hours in total. The results obtained are shown in Table 4. IL-2 productibility in a pH range of 4.8-6 increased 3-7.5 times over that obtained in constant temperature culture at 37° C., pH 7.0.

TABLE 4

Effect of Culture pH on IL-2 Productibility
(Changed-temperature culture)

| pH | IL-2 Productibility* |
|---|---|
| 4.5 | 10 |
| 4.8 | 300 |
| 5.0 | 530 |
| 5.5 | 750 |
| 6.0 | 510 |
| 6.5 | 180 |
| 7.0 | 130 |
| 7.5 | 60 |

*Indicated by percentage relative to the productibility obtained at 37° C., pH 7 in Table 3, Example 1"

EXAMPLE 3

Using the expression plasmid pTF4, which has a human IL-2 structural gene as an integrated element, E. coli strains 294, DH 1, W 3110 and C 600 were each transformed using the method shown in Example 1. Each resulting transformant was then inoculated into an original medium of the same composition as that in Example 1 and cultured at 37° for one night. Separately, 2.5 l of a medium prepared by adding 1 mg/l vitamin $B_1$ hydrochloride to M-9 medium was placed in 8 jar fermenters of 5 l capacity; the pH was adjusted to 5.5 in 4 of the fermenters and to 6.5 in the remaining 4. 125 ml of each of the transformants being cultured was used to inoculate the pH 5.5 and pH 6.5 media, and these were cultivated under the same conditions as in Example 2. The results are shown in Table 5.

TABLE 5

Effect of pH on IL-2 Productibility
of Various Transformants

| Transformant (E. coli) | pH 6.5 | pH 5.5 |
|---|---|---|
| 294/pTF4 | 100 | 200 |
| DH 1/pTF4 | 100 | 260 |
| W 3110/pTF4 | 100 | 310 |
| C 600/pTF4 | 100 | 280 |

In all transformants, the producibity at pH 5.5 increased 2 times or more over that obtained at pH 6.5." to the productibility at pH 5.5 is indicated as the percentage relative to the respective productibility at pH 6.5.

EXAMPLE 4

Eight media of different pH were prepared as in Example 1. Using each medium, cultivation was continued for 24 hours under the same temperature conditions as in Example 2, with the specified pH level kept constant using a 5N NaOH aqueous solution or 5N $H_2SO_4$. The results are shown in Table 6. IL-2 productibility in the pH range of 4.8-6 increased 5-7 times over that obtained at pH 7.0.

TABLE 6

Effect of pH on IL-2 Productibility
(pH adjuster: NaOH)

| pH | IL-2 Productibility |
|---|---|
| 4.5 | 20 |
| 4.8 | 275 |
| 5.0 | 560 |
| 5.5 | 725 |
| 6.0 | 530 |
| 6.5 | 210 |
| 7.0 | 100 |
| 7.5 | 35 |

*Indicated as percentage relative to the productibility obtained at pH 7.0.

EXAMPLE 5

Bacterial cells were collected by centrifugation from each culture liquid (pH 5.5 or 7.0) obtained in Example 2, and then frozen at −80° C. Twelve grams of each of the frozen cells was uniformly suspended in 100 ml of an extract (pH 7.0) containing 7M guanidine hydrochloride and 0.1M Tris-HCl (pH 7.0), and stirred at 4° C. for 1 hour. Each resulting lysate was then centrifuged at 28.000×g for 20 minutes, yielding a supernatant. Each resulting supernatant, after dialyzation with a 0.01M Tris-HCl buffer solution (pH 8.5), was centrifuged at 19,000×g for 10 minutes, yielding a dialysis supernatant. Each resulting dialysis supernatant was passed through a column packed with DE 52 (DEAE cellulose, Whatman, UK) equilibrated with a 0.01M Tris-HCl buffer solution (pH 8.5) to adsorb protein; IL-2 was then eluted using a linear NaCl concentration gradient (0.015M NaCl, 1 l). Each resulting active fraction, after being concentrated to approx. 5 ml using a YM-5 membrane (Amicon Co., USA), was subjected to gel filtration using a column (500 ml capacity) packed with Sephacryl S-200 (Pharmacia, Sweden) equilibrated with a 0.1M Tris-HCl (pH 8.0)-1M NaCl buffer solution. Each of the resulting concentrates was adsorbed in an Ultrapore RPSC column (Altex Co., USA), and subjected to HPLC using a trifluoroacetic acid-acetonitrile system as eluent.

The following conditions were maintained:

Column: Ultrapore RPSC (4.6×75 mm)

Column temperature: 30° C.

Eluent A: trifluoroacetic acid (0.1%) to water (9.99%)

Eluent B: trifluoroacetic acid (0.1% to acetonitrile (99.9%) acetonitrile

Elution program: 0 min. (68% A=32% B)—25 min. (55% A+45% B)—35 min. (45% A+55% B)—45 min. (30% A+70% B)—48 min. (100% B)

Elution rate: 0.8 ml/min.

Detection wavelength: 230 nm

An active fraction of approx. 39 min. retention time was thus collected and subjected to freeze-drying, yielding human IL-2 protein in the form of a white powder.

The yield from bacterial cells cultured at pH 7.0 was 5.2 mg, while that from cells cultured at pH 5.5 was 12.7 mg. It was determined that protein purity was 99% (measured by densitometry) in both cases, and that there was no difference in protein chemical characteristics between the two.

REFERENCE EXAMPLE

*Escherichia coli* C-4 strain was obtained from the *E. coli* C-4/pTF4 strain cells obtained in Example 1, by plasmid curing with ethidium bromide in accordance with the method of Bouanchaud et al. [Journal of General Microbiology, Vol. 54, p. 417 (1968)].

What is claimed is:

1. In a method for producing interleukin-2 which comprises cultivating a transformant of *Escherichia coli* capable of producing interleukin-2 in a medium, the improvement comprising:

inoculating said *Escherichia coli* into the medium at a pH in the range from about 4.8 to 6.0 and growing said *Escherichia coli* in the said medium while maintaining the pH in the 4.8 to 6.0 range.

2. The method according to claim 1, wherein the transformant contains DNA coding for interleukin-2, said interleukin-2 comprising the amino acid sequence of No. 1 to No. 133 in FIG. 1, or DNA coding for another polypeptide having the physiological activity of interleukin-2.

3. The method according to claim 2, wherein the DNA codes for interleukin-2 having the amino acid sequence of No. 1 to No. 133 in FIG. 1.

4. The method according to claim 2, wherein the transformant contains at least one promoter upstream from the DNA.

5. The method according to claim 4, wherein the promoter is a tryptophane promoter.

6. The method according to claim 1, wherein the *Escherichia coli* is originated from *Escherichia coli* K-12.

7. The method according to claim 1, wherein the pH is from about 5.0 to 5.8.

8. The method according to claim 1, which further comprises maintaining the pH range of the medium by the addition of an inorganic base.

9. The method according to claim 8, wherein the inorganic base is aqueous ammonia.

10. The method according to claim 1, wherein the medium is an M-9 medium, further containing glucose and casamino acid.

11. The method according to claim 1, wherein the growing is conducted under aeration with agitation.

12. The method according to claim 1, wherein the medium is maintained at a temperature of about 37° C. until the middle stage of the growth and then lowered to a temperature in the range of from 20° to 30° C.

13. The method of claim 4, wherein the transformant contains from one to three promoters upstream from the DNA.

14. The method of claim 13, wherein the promoters are tryptophane promoters.

* * * * *